(12) United States Patent
Ushizawa et al.

(10) Patent No.: US 7,759,072 B2
(45) Date of Patent: Jul. 20, 2010

(54) IMMUNOASSAY METHOD AND REAGENT THEREFOR

(75) Inventors: Koji Ushizawa, Ryugasaki (JP); Michiko Kawamoto, Ryugasaki (JP); Shoko Yamamoto, Ryugasaki (JP); Kumiko Yuki, Ryugasaki (JP); Yoko Ikeda, Ryugasaki (JP); Mitsuaki Yamamoto, Ryugasaki (JP)

(73) Assignee: Sekisui Medical Co., Ltd., Tokyo (JP)

( * ) Notice: Subject to any disclaimer, the term of this patent is extended or adjusted under 35 U.S.C. 154(b) by 127 days.

(21) Appl. No.: 11/817,515

(22) PCT Filed: Mar. 2, 2006

(86) PCT No.: PCT/JP2006/303978

§ 371 (c)(1),
(2), (4) Date: Aug. 31, 2007

(87) PCT Pub. No.: WO2006/093224

PCT Pub. Date: Sep. 8, 2006

(65) Prior Publication Data

US 2009/0035785 A1    Feb. 5, 2009

(30) Foreign Application Priority Data

Mar. 3, 2005 (JP) .............................. 2005-059205

(51) Int. Cl.
*G01N 33/53* (2006.01)

(52) U.S. Cl. ........................ 435/7.1; 435/90.1; 435/90.2
(58) Field of Classification Search .................. None
See application file for complete search history.

(56) References Cited

U.S. PATENT DOCUMENTS

| 4,238,565 A | 12/1980 | Hornby et al. |
| 5,445,942 A | 8/1995 | Rabin et al. |

FOREIGN PATENT DOCUMENTS

| EP | 0 051 213 | 5/1982 |
| EP | 0 327 918 | 8/1989 |
| JP | 55 002997 | 1/1980 |
| JP | 64 063862 | 3/1989 |
| JP | 02 147862 | 6/1990 |
| JP | 09 070297 | 3/1997 |
| JP | 2004 173519 | 6/2004 |
| WO | WO 97/27474 | 7/1997 |

*Primary Examiner*—Jacob Cheu
(74) *Attorney, Agent, or Firm*—Oblon, Spivak, McClelland, Maier & Neustadt, L.L.P.

(57) ABSTRACT

The present invention provides a novel immunoassay method with high reaction specificity and high sensitivity. The present invention also provides a method for immunoassaying a target antigen utilizing reactivation of an apoenzyme, which includes simultaneously or sequentially adding a test sample to an antibody specific to the target antigen, the target antigen labeled with a coenzyme, an apo-D-amino acid oxidase, a D-amino acid, and a reagent for detecting a hydrogen peroxide produced by the oxidase.

24 Claims, 4 Drawing Sheets

Tes : Testosterone

IMMUNOASSAY METHOD AND REAGENT THEREFOR

CROSS-REFERENCE TO RELATED APPLICATIONS

The present application is a 35 U.S.C. §371 National Stage patent application of International patent application PCT/JP06/303978, filed on Mar. 2, 2006, which claims priority to Japanese patent application JP 2005-059205, filed on Mar. 3, 2005.

TECHNICAL FIELD

The present invention relates to a method of immunoassaying a target antigen wherein not only high-molecular compounds such as polysaccharides and proteins (e.g. glycosylated protein) but also low-molecular compounds such as hormones and peptides can be detected with high sensitivity, and a reagent composition therefor.

BACKGROUND ART

An immunoassay method utilizing reactivation of an apoenzyme is known as one of homogeneous competitive enzyme immunoassay (EIA) methods which are useful as methods for detecting low-molecular compounds such as hormones and peptides with high sensitivity. In the immunoassay method, glucose oxidase requiring flavin adenine dinucleotide (FAD) as a coenzyme is conventionally used as an apoenzyme (Patent Document 1, Non-Patent Documents 1 to 3).

However, as described in Non-patent Document 3, the detection limit of trinitrotoluene in the method using glucose oxidase is 5 μg/L (5 ng/mL), that is, the method has a problem that only limited targets can be assayed therewith due to its insufficient sensitivity.

Furthermore, there are also problems that a blank can be varied because the apoenzyme can react with not only glucose added as a substrate but also endogenous substrates or coenzymes such as glucose or free FAD derived from a test sample, resulting in reaction between a detection reagent and hydrogen peroxide produced nonspecifically, and the like.

[Patent Document 1] JP-A-55-2997
[Non-Patent Document 1] Anal. Chem., 1981, 658-665
[Non-Patent Document 2] Meth. Enzymol., 1983, 413
[Non-Patent Document 3] Fresenius J. Anal. Chem., 1998, Vol. 361, 174-178

DISCLOSURE OF THE INVENTION

Problems to be Solved by the Invention

An object of the present invention is to provide a novel immunoassay method with high reaction specificity and high sensitivity.

Means for Solving the Problems

The inventors of the present invention found that reaction specificity of an immunoassay method utilizing reactivation of an apoenzyme could be improved by using apo-D-amino acid oxidase, which has not been conventionally used, and using a D-amino acid, which rarely exists in a living body, as a substrate, and that the assay can be modified in response to the quantity of the target antigen present in a test sample since assay sensitivity can be controlled by selecting the type of the D-amino acid, and thus accomplished the present invention.

That is, the present invention provides the following:

(1) A method of immunoassaying a target antigen utilizing reactivation of an apoenzyme, wherein the method includes simultaneously or sequentially adding to a test sample an antibody specific to the target antigen, the target antigen labeled with a coenzyme, an apo-D-amino acid oxidase, one or more D-amino acids, and a reagent for detecting a hydrogen peroxide produced from the one or more D-amino acids using the apo-D-amino acid oxidase activated by the coenzyme.

(2) The immunoassay method according to (1), wherein immunoassay sensitivity is modified by selecting the one or more D-amino acids.

(3) The immunoassay method according to (1) or (2), wherein the one or more D-amino acids are selected from the group consisting of D-forms of Ala, Met, Val, Ile, Phe, Pro, Ser, Thr, Asn, Leu, Tyr, Tm, Asp, Glu, His, and Arg.

Furthermore, the present invention provides the following:

(4) A reagent composition for immunoassay, including an antibody specific to the target antigen, the target antigen labeled with a coenzyme, an apo-D-amino acid oxidase, one or more D-amino acids, and a reagent for detecting a hydrogen peroxide produced from the one or more D-amino acids using the apo-D-amino acid oxidase activated by the coenzyme.

(5) The reagent composition for immunoassay according to (4), wherein assay sensitivity is modified by selecting the type of the D-amino acid to be used.

(6) The reagent composition for immunoassay according to (4) or (5), wherein one or more D-amino acids selected from a group consisting of D-forms of Ala, Met, Val, Ile, Phe, Pro, Ser, Thr, Asn, Leu, Tyr, Trp, Asp, Glu, His, and Arg are used as the D-amino acid.

Effect of the Invention

High reaction specificity can be achieved by using the D-amino acid oxidase of the present invention without influence of endogenous substrates since D-amino acids used as substrates are amino acids that rarely exist in an organism. Furthermore, assay sensitivity can be controlled by selecting the types of the D-amino acids. Therefore, the assay can be modified in response to the quantity of a target antigen present in a test sample. The method of the present invention is useful particularly for assaying low-molecular compounds such as hormones and peptides.

BEST MODE FOR CARRYING OUT THE INVENTION

Apo-D-amino acid oxidase used in the present invention, whose existence and function were elucidated in the 1960s, is an apo-form of D-amino acid oxidase, which specifically oxidizes D-amino acids. Apo-D-amino acid oxidase extracted and purified from the porcine kidneys is known and can be suitably used. For example, those commercially available from Calzyme, Inc. can be used, and those obtained with gene recombination techniques may also be used. Furthermore, as examples of the enzyme derived from microorganisms, those derived from a strain in which the D-amino acid oxidase gene derived from *Trigonopsis variabilis* is expressed (refer to A. Isoai et al., Biotechnology and Bioengineering, Vol. 80, No. 1, 22-32 [Oct. 5, 2002]), those derived from *Fusariume quiseti* (refer to T. Esaki et al., Flavins and Flavoproteins, 1993), and the like are known.

Figure 1:
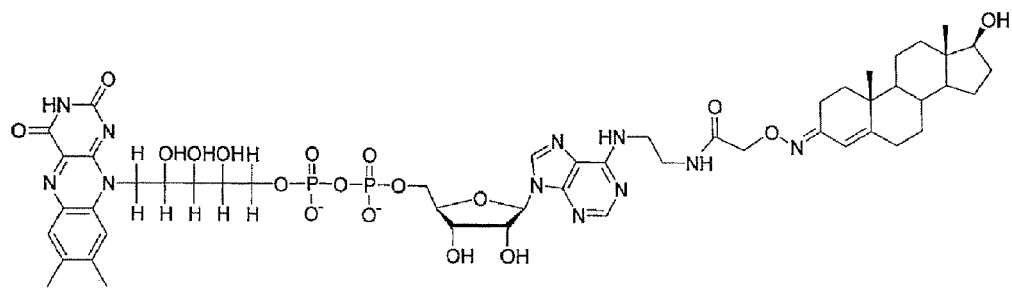
FIG. 1 is the structural formula of FAD-labeled testosterone.

A coenzyme of the above-mentioned D-amino acid oxidase is a flavin dinucleotide, more specifically flavin adenine dinucleotide (FAD). An antigen can be labeled with a coenzyme according to the method described in the above-mentioned Non-patent Document 3, the method of D. L. Morris et al. (Analytical Chemistry, 53, pp 658-665 [1981]), the method of T. J. Richard et al. (Clinical Chemistry, 27, pp 1499-1504 [1981]), the methods described in JP-A-55-2996 and the like, for example. FIG. 1 shows an FAD-labeled testosterone-3-CMO as an example of a FAD-labeled antigen.

The binding site of the coenzyme and an antigen is preferably selected so that the site does not inhibit binding reaction of an antibody and the antigen.

Examples of the antigen include low-molecular compounds such as low-molecular proteins, hormones, peptides, vitamins and drugs. Specific examples of the low-molecular proteins include insulin and renin. Specific examples of the hormones include: triiodine thyronine (T3), serum total thyroxine (T4) and so forth as thyroid gland-related hormones; 17-hydroxycorticoide (OHCS), cortisol, aldosterone, corticosterone, 18-OH-deoxycorticosterone (18-OH-DOC), dihydroepiandrosterone sulfate (DHEA-S), androstenedione, pregnenolone, and so forth as adrenal cortex-related hormones; three estrogen fractions (estrone, estradiol, estriol), HCG, progesterone, pregnanediol, testosterone, 5α-dihydrotestosterone, and so forth as sex gland/placenta-related hormones; angiotensin I, angiotensin II, cyclic AMP, cyclic CMP, endothelin-1, histamine, carnitine fraction, and so forth as peptide/amino acid-related hormones. Specific examples of peptides include BNP and the like. Specific examples of vitamins include folic acid, vitamin A, β-carotin, B-complex vitamins, vitamin C (ascorbic acid), 1,25-$(OH)_2$ vitamin D, vitamin E, nicotinic acid (niacin), and so forth. Specific examples of bone metabolism-related substances include osteocalcin, urine deoxypyridinoline, and so forth. Specific examples of drugs include antiepileptic drugs such as phenobarbital, primidone, phenytoin, carbamazepine, valproic acid, zonisamide, trimethadione, clonazepam, nitrazepam, diazepam, and acetazolamide; psychoneurotic drugs such as haloperidol and bromperidol; cardiotonic drugs such as digoxin and digitoxin; antiarrhythmic drugs such as lidocaine, chinidine, procainamide, N-acetylprocainamide, aprindine, and propranolol; antibiotic preparations such as gentamicin, tobramycin, vancomycin, and amikacin; acetaminophen; cyclosporin; tacrolimus; methotrexate; theophylline; ribavirin, and so forth.

Examples of a test sample containing the antigen include blood, serum, plasma, urine, sweat, tear, saliva, sperm, and vaginal secretion, as well as those extracted or secreted from mucous membrane, mucosal cells, bone marrow, hair, and the like.

Any antibody may be used so long as it is an antibody specific to the target antigen, and either a monoclonal antibody or a polyclonal antibody may be used. When the target antigen is a low-molecular compound such as a hormone or a peptide, any techniques such as a method in which an antibody is obtained by immunization using the antigen bound to a high-molecular compound such as bovine serum albumin (BSA) or keyhole limpet hemocyanin (KLH), or a phage display method can be employed as required.

Various D-amino acids can be used as a D-amino acid used as a substrate of the D-amino acid oxidase, and D-forms of amino acids constituting a peptide are preferred. Specific examples thereof include D-forms of amino acids such as Ala, Met, Val, Ile, Phe, Pro, Ser, Thr, Asn, Leu, Tyr, Trp, Asp, Glu, His, and Arg. Sensitivity of the assay can be modified in response to the quantity of a target antigen present in a test sample by suitably selecting the type of the D-amino acids.

Figure 2:
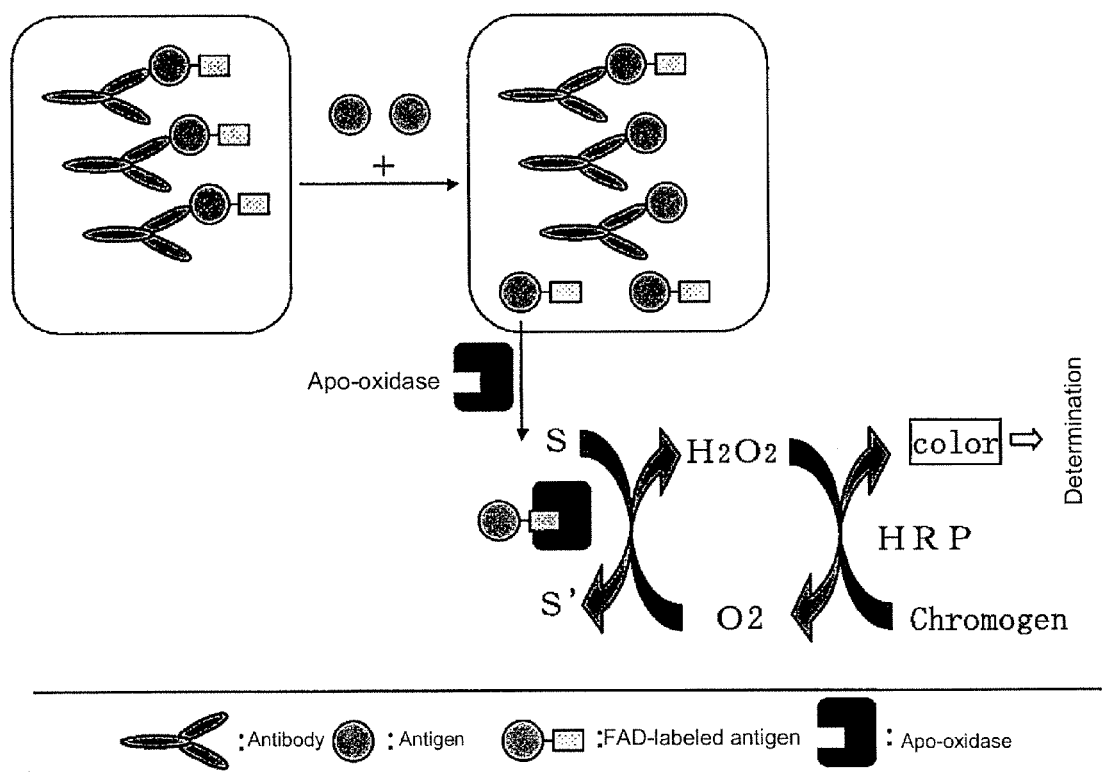
FIG. 2 shows a reaction system model using a peroxidase and an oxidizable coloring reagent as reagents for detecting hydrogen peroxide.

Reagents for detecting hydrogen peroxide produced from the one or more D-amino acids using the apo-D-amino acid oxidase activated by the coenzyme can be suitably selected from reagents for electrode methods and reagents for colorimetric methods. The reagents for electrode methods are reagents for detecting hydrogen peroxide with an electrode and include peroxidase. The reagents for colorimetric methods are reagents for measuring changes in the level of chromogens corresponding to the quantity of hydrogen peroxide using an absorption spectrometer and include peroxidase and chromogen. As a colorimetric method, a method using a peroxidase and an oxidizable coloring reagent is generally known, and the method can be suitably used. For example, as an assay system applicable to an automated analyzer, Trinder coloring reagents are commonly used, while single-molecular coloring reagents such as TPM-PS and TMBZ-PS can also be used. The reagents can be used not only in colorimetric assays as described above but also in fluorescent or luminescent assays. If an antibody is immobilized on a membrane beforehand and using it in a similar reaction system, these reagents can also be used as POCT reagents. FIG. 2 shows a reaction system model using a peroxidase and an oxidizable coloring reagent as reagents for detecting hydrogen peroxide produced from the one or more D-amino acids using the apo-D-amino acid oxidase activated by the coenzyme.

In FIG. 2, a FAD-labeled antigen is firstly bound to an antibody. Then, when another antigen is added to compete the FAD-labeled antigen, the FAD-labeled antigen is released as a result of the difference in affinity, and the FAD moiety of the released antigen binds to apo-D-amino acid oxidase. The apo-D-amino acid oxidase exhibits an enzyme activity by binding to the FAD-labeled antigen, and a D-amino acid, a substrate, is thereby oxidized, resulting in the generation of hydrogen peroxide. Thereafter, a reaction by peroxidase using hydrogen peroxide is proceeded, which causes coloration of the oxidizable coloring reagent, and the concentration of the antigen can be finally determined by measuring the degree of coloration.

In the immunoassay method of the present invention, the above-described components and reagents may be simultaneously reacted or sequentially reacted by adding them sequentially. It is sufficient that the reaction temperature is at about 5 to 40° C. For a reaction, various buffers such as, for example, Tris-HCl buffer, phosphate buffer, and Good's buffer can be used, and the buffer can be selected depending on the property of the reagent composition. An exemplified assay method may includes adding a sample to a FAD-labeled target antigen, contacting the mixture with an antibody specific to the antigen, reacting a free FAD-labeled target antigen with an apo-D-amino acid oxidase, producing a hydrogen peroxide from a D-amino acid using a D-amino acid oxidase activated by FAD, applying the hydrogen peroxide to a detection system containing a peroxidase and an oxidizable coloring reagent to cause a reaction among them, and determining the change in absorbance using a spectrophotometer. For the sequential reaction with an automated analyzer or the like, it is preferable to admix (1) a sample, (2) reagents including a FAD-labeled target antigen, an antibody against the target antigen, and an oxidizable coloring reagent (R1), and (3) reagent (R2) including an apo-D-amino acid oxidase and a peroxidase in this order to react.

The immunoassay method of the present invention is preferably a homogeneous competitive EIA method and can be applied to an automated analyzer. For example, when a Hitachi 7170 automated analyzer is used, the methods can be applicable by suitably selecting the wavelength for determination depending on the oxidizable coloring reagent to be used, setting the amount of a sample as 15 µl, the amount of an aliquot of the reagent (R1) as 150 µl, the amount of an aliquot of the reagent (R2) as 75 µl, and measuring the data at the measurement points as 16-34 in an endpoint determination method using a two-point end-mode. However, the above-mentioned amounts of the sample and the aliquots of reagents are not limited to these examples and can be suitably set depending on the reagent composition.

So long as the immunoassay reagent of the present invention contains the above-described components, the reagent may be supplied in the form of a solution, or all or a part of the component of the reagent may be supplied in the form of a lyophilized product to be used for finally preparing the reagent by dissolving the lyophilized product with a solvent, wherein the composition can be contained in either the lyophilized product or the solvent, or both thereof.

EXAMPLES

The present invention will be described in more detail by way of the following Examples. However, the scope of the present invention is not limited thereto.

Example 1

Figure 3:
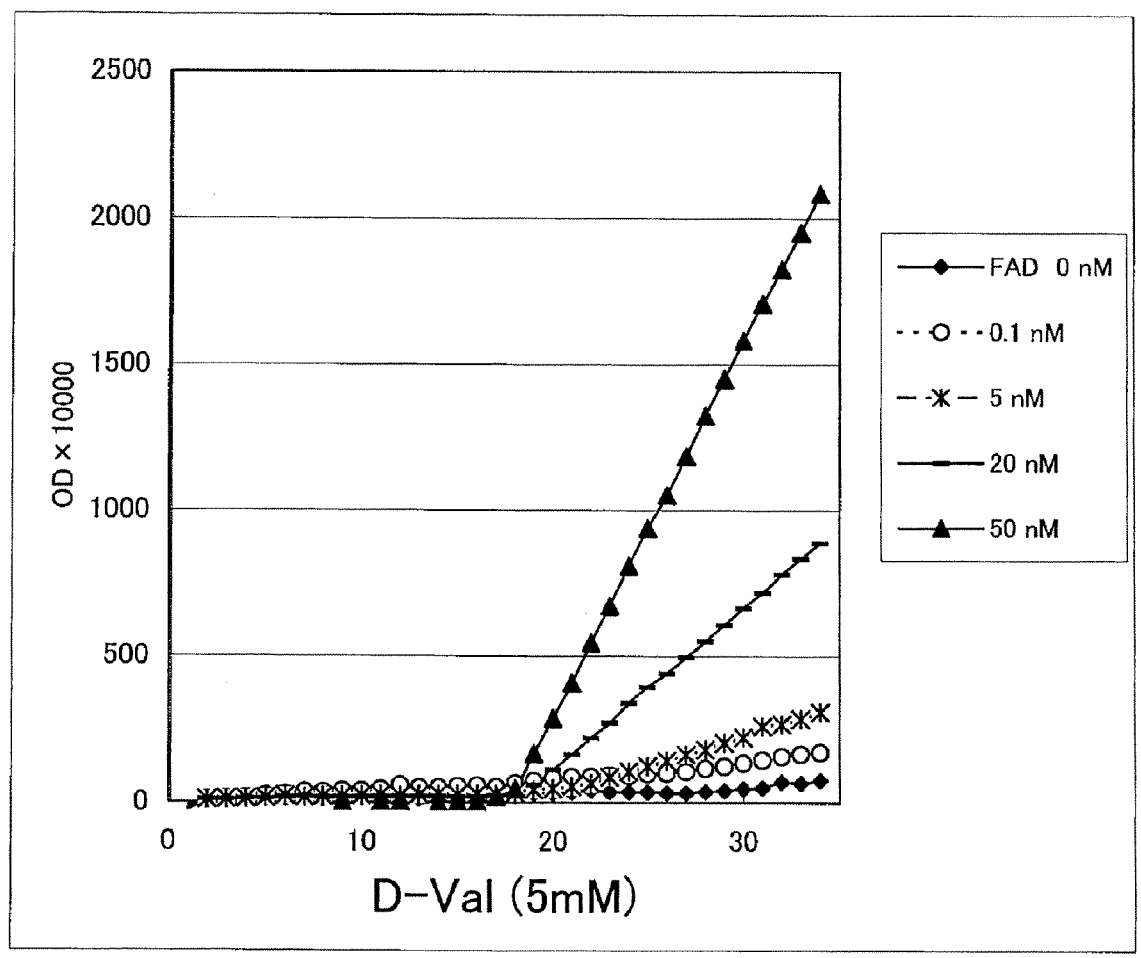
FIG. 3 shows the reaction time course when D-valine was used as a D-amino acid.
Figure 4:
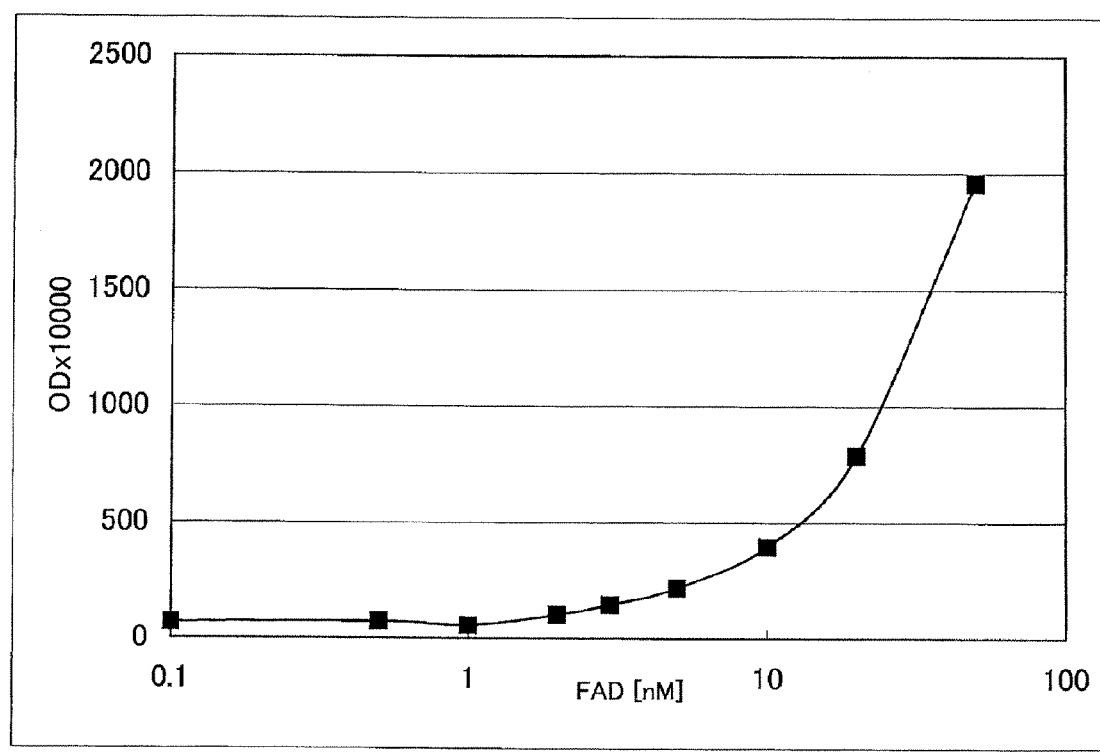
FIG. 4 shows a calibration curve when D-valine was used as a D-amino acid.

1) Confirmation of Activation of Apo-D-Amino Acid Oxidase by FAD and its Substrate Specificity Reagent 1 containing 50 mM Tris-HCl (pH 8.3), 5 mM DA-64 (Wako Pure Chemical Industries), and 5 mM D-amino acid, reagent 2 containing 10 U/ml apo-D-amino acid oxidase (Calzyme Inc., Catalog No. 176A0025) and 5 U/ml peroxidase, and aqueous FAD solution as a sample were applied to a Hitachi 7170 automated analyzer at a setting of two-point end-mode and using a parameters of 7 µl for a sample, 180 µl for R1, 90 µl for R2, and 700 nm for a wavelength for determination. The reaction time course and calibration curve when using D-valine as a D-amino acid are shown in FIGS. 3 and 4, respectively.

2) Comparison of Reactivity Between Various D-Amino Acids

As in 1), the activity of the reconstituted apoenzyme was confirmed. Assays only varying types of the D-amino acids were then performed. As D-amino acids, D-forms of Ala, Met, Val, Ile, Phe, Pro, Ser, Thr, Asn, Leu, Tyr, Trp, Asp, Glu, His, and Arg were each used. The percent reactivities of the above-mentioned various D-amino acids were calculated to the value of D-valine which was defined as 100. The results are listed in Table 1.

Table 1 shows that the relative reactivity of the enzyme to a substrate varies depending on the type of the D-amino acid used. It was found that assay sensitivity could be controlled by utilizing this property.

TABLE 1

|  | (%) |
|---|---|
| D-Val | 100 |
| D-Ala | 136 |
| D-Arg | 8 |
| D-Leu | 97 |
| D-Met | 322 |
| D-Phe | 170 |
| D-Pro | 374 |
| D-Ser | 117 |
| D-Trp | 14 |
| D-Tyr | 159 |
| D-Ile | 178 |

Example 2

Detection of Testosterone Using Anti-Testosterone Antibody

Figure 5:
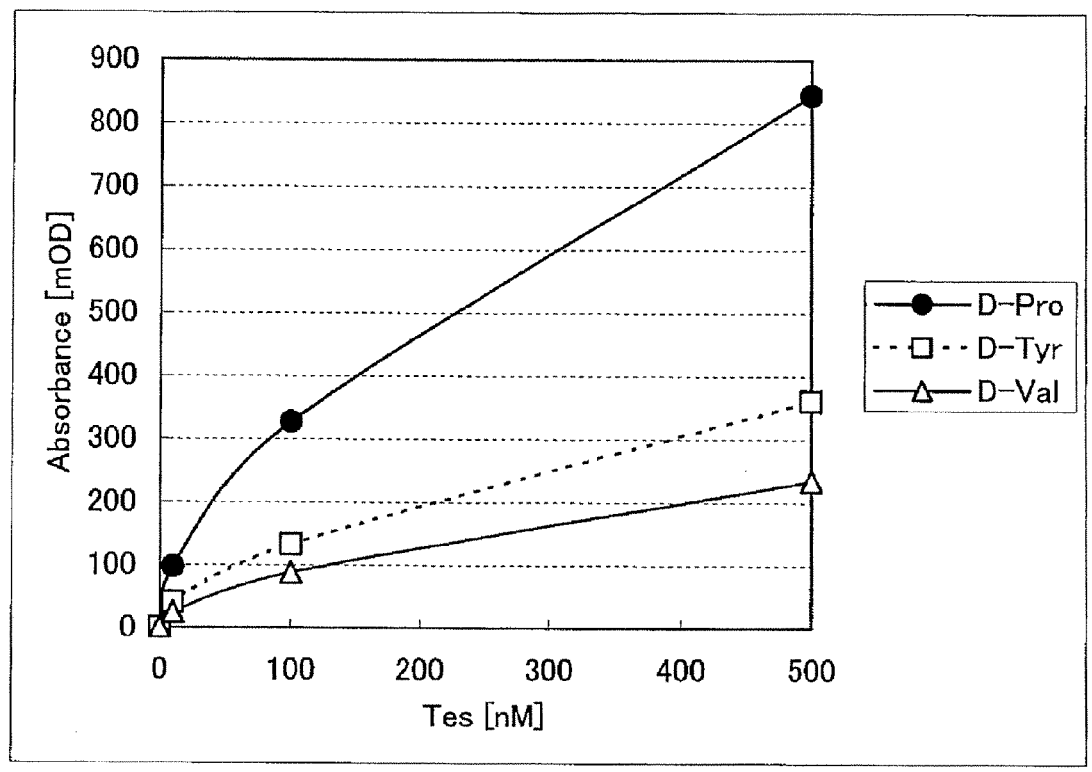
FIG. 5 shows a calibration curve when testosterone was assayed by the method of the present invention.

The reagent 1 of Example 2 was prepared by adding µM FAD-labeled testosterone and 1 mg/ml of antibody against testosterone (BiosPacific, Clone No.: A53070148P) to Reagent 1 of Example 1 wherein D-valine, D-tyrosine or D-proline was used as D-amino acid. Reagent 2 identical to the one in Example 1 was used. An assay was performed with a Hitachi 7170 automated analyzer, by setting the amount of the sample as 15 µl, the amount of an aliquot of reagent R1 as 150 µl, the amount of an aliquot reagent as 75 µl, using endpoint determination method under two-point end-mode, the measurement points as 16-34 and the measurement wavelength as 700 nm. The calibration curve when testosterone was used as the sample is shown in FIG. 5. As shown in FIG. 5, a favorable calibration curve was obtained, which indicating that assay sensitivity can be controlled by changing the type of the D-amino acid.

The invention claimed is:

1. A method for immunoassaying a target antigen comprising:
   contacting a test sample with
      an antibody specific to the target antigen,
      the target antigen labeled with a flavin dinucleotide coenzyme,
      an apo-D-amino acid oxidase,
      one or more D-amino acids, and
      a reagent for detecting a hydrogen peroxide produced from the one or more D-amino acids using the apo-D-amino acid oxidase activated by the coenzyme; and
   detecting the amount of hydrogen peroxide produced, wherein the amount of hydrogen peroxide correlates with the amount of the target antigen in the test sample.

2. The immunoassay method according to claim 1, further comprising adjusting immunoassay sensitivity by selecting one or more specific D-amino acids based on the quantity of target antigen in a test sample.

3. The immunoassay method according to claim 1, wherein the one or more D-amino acids are selected from the group consisting of D-forms of Ala, Met, Val, Ile, Phe, Pro, Ser, Thr, Asn, Leu, Tyr, Trp, Asp, Glu, His, and Arg.

4. The immunoassay method of claim 1, wherein the test sample is blood, serum or plasma.

5. The immunoassay method of claim 1, wherein the test sample is urine, sweat, tears, saliva, sperm or a vaginal secretion.

6. The immunoassay method of claim 1, wherein the test sample is extracted or secreted from a mucous membrane, mucosal cells, bone marrow, or hair.

7. The immunoassay method of claim 1, wherein the target antigen is a polysaccharide.

8. The immunoassay method of claim 1, wherein the target antigen is a glycosylated protein.

9. The immunoassay method of claim 1, wherein the target antigen is a peptide.

10. The immunoassay method of claim 1, wherein the target antigen is a hormone, vitamin or drug.

11. The immunoassay method of claim 1, wherein the coenzyme is a flavin adenine dinucleotide (FAD).

12. The immunoassay method of claim 1, wherein the antibody is a monoclonal antibody.

13. The immunoassay method of claim 1, which comprises an electrode method for detecting hydrogen peroxide and a suitable reagent for detecting hydrogen peroxide usable in said method.

14. The immunoassay method of claim 1, which comprises a colorimetric method for detecting hydrogen peroxide and a suitable reagent for detecting hydrogen peroxide usable in said method.

15. The immunoassay method of claim 1, wherein the components are simultaneously added to the test sample.

16. The immunoassay method of claim 1, wherein the components are sequentially added to the test sample.

17. The immunoassay method of claim 1, which is a homogeneous competitive EIA method.

18. An immunoassay reagent composition comprising:
an antibody specific to a target antigen,
a target antigen labeled with a flavin dinucleotide coenzyme,
an apo-D-amino acid oxidase,
one or more D-amino acids, and
a reagent for detecting a hydrogen peroxide produced from the one or more D-amino acids using the apo-D-amino acid oxidase activated by the coenzyme.

19. The immunoassay reagent composition of claim 18, wherein the antibody is a monoclonal antibody.

20. The immunoassay reagent composition of claim 18, wherein the target antigen is a polysaccharide, glycosylated protein, peptide, hormone, vitamin or drug.

21. The immunoassay reagent composition of claim 18, wherein the coenzyme is a flavin adenine dinucleotide (FAD).

22. The immunoassay reagent composition of claim 18, wherein the one or more D-amino acids are selected from D-forms of Ala, Met, Val, Ile, Phe, Pro, Ser, Thr, Asn, Leu, Tyr, Trp, Asp, Glu, His, and Arg.

23. The immunoassay reagent composition of claim 18, wherein the reagent for detecting hydrogen peroxide is suitable for use in an electrode method.

24. The immunoassay reagent composition of claim 18, wherein the reagent for detecting hydrogen peroxide is suitable for use in a colorimetric method.

* * * * *